(12) United States Patent
Corma Canós et al.

(10) Patent No.: US 9,199,955 B2
(45) Date of Patent: Dec. 1, 2015

(54) PRODUCTION OF LIQUID FUELS (SYLVAN-LIQUID-FUELS) FROM 2-METHYLFURAN

(75) Inventors: Avelino Corma Canós, Valencia (ES); Michael Renz, Valencia (ES); Olalla De La Torre Alfaro, Valencia (ES)

(73) Assignees: CONSEJO SUPERIOR DE INVESTIGACIONES CIENTIFICAS (CSIC), Madrid (ES); UNIVERSIDAD POLITECNICA DE VALENCIA (UPV), Valencia (ES)

( * ) Notice: Subject to any disclaimer, the term of this patent is extended or adjusted under 35 U.S.C. 154(b) by 805 days.

(21) Appl. No.: 13/491,910

(22) Filed: Jun. 8, 2012

(65) Prior Publication Data

US 2012/0316372 A1    Dec. 13, 2012

Related U.S. Application Data

(63) Continuation of application No. PCT/ES2010/070811, filed on Dec. 7, 2010.

(30) Foreign Application Priority Data

Dec. 11, 2009 (ES) .................................. 200902375

(51) Int. Cl.
| | | |
|---|---|---|
| C10G 1/00 | (2006.01) |
| C07C 27/00 | (2006.01) |
| C10L 1/00 | (2006.01) |
| C07D 307/38 | (2006.01) |
| C10G 3/00 | (2006.01) |

(52) U.S. Cl.
CPC ............... C07D 307/38 (2013.01); C10G 3/42 (2013.01); C10G 3/45 (2013.01); C10G 3/47 (2013.01); C10G 3/50 (2013.01)

(58) Field of Classification Search
CPC .. C07D 307/38; C07D 307/12; C07D 307/14; C07D 307/44; C10G 3/42; C10G 3/47; C10G 3/50
See application file for complete search history.

(56) References Cited

U.S. PATENT DOCUMENTS

| | | | |
|---|---|---|---|
| 2008/0216391 A1* | 9/2008 | Cortright et al. ................ | 44/307 |
| 2010/0218417 A1* | 9/2010 | Bauldreay et al. .............. | 44/438 |
| 2011/0201832 A1* | 8/2011 | Li et al. ......................... | 549/505 |

FOREIGN PATENT DOCUMENTS

ES     2362248 A1 *  6/2011

OTHER PUBLICATIONS

"Synthesis of Transportation Fuels from Biomass: Chemistry, Catalysts and Engineering" by George W. Huber, Sara Iborra and Avelino Corma, Chem. Rev. (2006) 106 pp. 4044-4098.*
EIC Search 13491910-492294.*

* cited by examiner

*Primary Examiner* — Pamela H Weiss
(74) *Attorney, Agent, or Firm* — Wenderoth, Lind & Ponack, L.L.P.

(57) ABSTRACT

The present invention describes a procedure for the production of liquid fuel having a content high in alkanes and low in oxygenated compounds, comprising as a minimum: a first step of alkylation of 2-methylfuran (commonly denominated Sylvan) with a furan alcohol 2 having the formula: (2), wherein $R^1$ is H or an aliphatic or aromatic or heteroaromatic moiety, $R^2$ is H or an aliphatic or aromatic or heteroaromatic moiety, and $R^3$ is H, hydroxymethyl or an aliphatic or aromatic or heteroaromatic moiety, in the presence of a catalyst, a second step of hydrogenation and dehydration of the compound obtained in step 1 in the presence of hydrogen, utilizing suitable hydrogenation and dehydration catalysts.

22 Claims, 1 Drawing Sheet

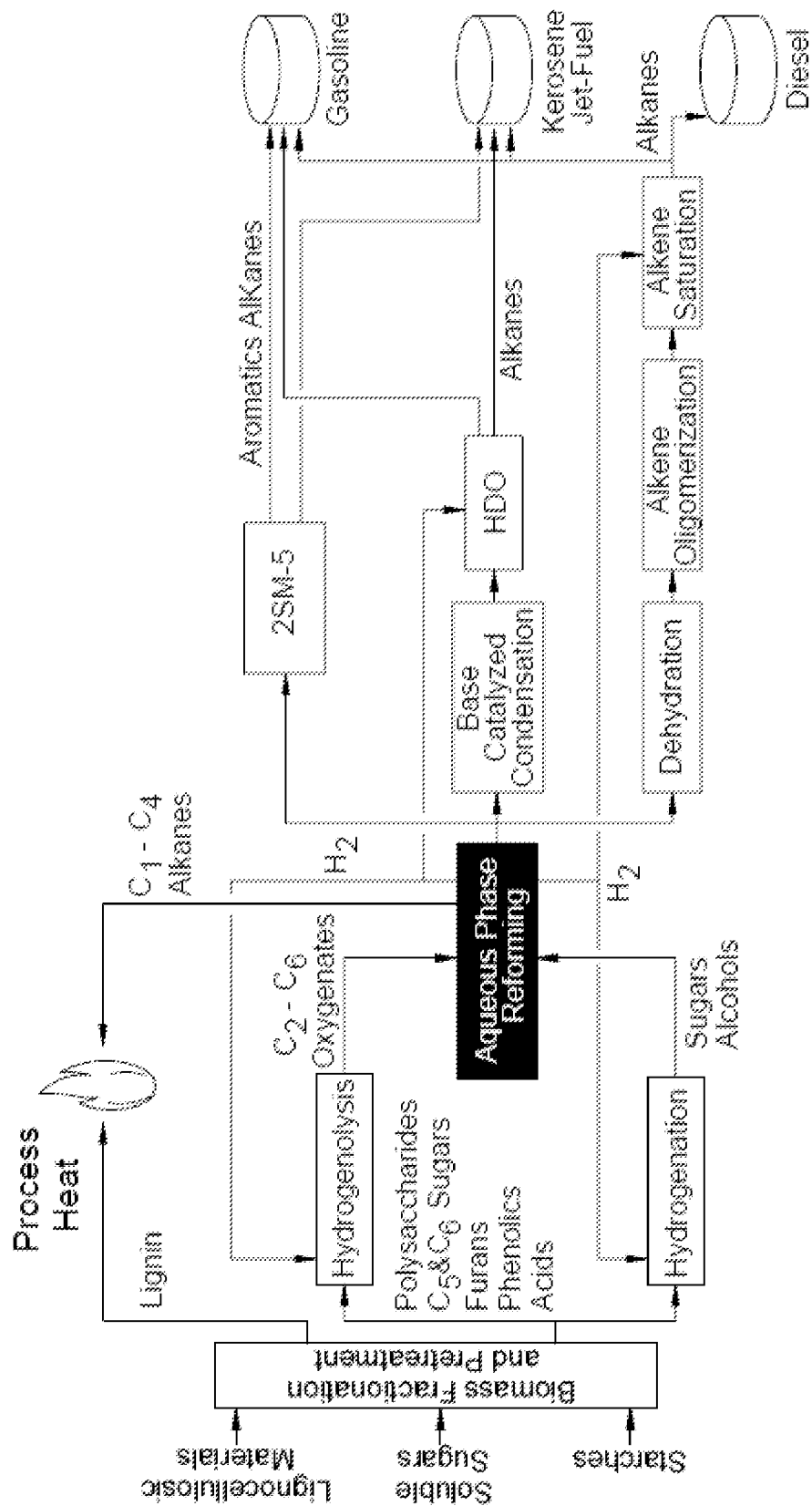

PRODUCTION OF LIQUID FUELS (SYLVAN-LIQUID-FUELS) FROM 2-METHYLFURAN

This application is a Continuation of International Application No. PCT/ES2010/070811, filed Dec. 7, 2010.

FIELD OF THE INVENTION

This invention belongs to the field of conversion of plant biomass into transport fuels.

BACKGROUND ART

Biofuels are fuels of plant origin, which have characteristics similar to fossil fuels, and this allows their use in barely modified engines. These fuels have several environmental advantages. In the case that the biofuels are of plant origin, the balance of carbon dioxide in its combustion is neutral since it can be considered that the same amount of carbon dioxide produced in said combustion, has been previously consumed from the carbon dioxide from the atmosphere through photosynthesis cycles (over a period of years). In addition, biofuels do not contain the element nitrogen or the element sulfur. For this reason, the oxides of these elements will not be produced in its combustion, thus preventing the formation of nitrous gases responsible for skin irritation and damage to the respiratory system and the origin of the tropospheric ozone and smog formation. It is known that these oxides promote the acid rain formation, being sulphur oxides the main cause of the same.

The first-generation of transport biofuels forms mainly biodiesel (along with bio-ethanol). Today, methyl and ethyl esters of fatty acids referred to as biodiesel (or FAMEs). Biodiesel is obtained by transesterification of vegetable oils with methanol or ethanol. This biofuel has some disadvantages. Since it is not a hydrocarbon, it is not interchangeable with the current diesel. This means that engines and/or vehicles need an adaptation to be able to use 100% biodiesel as fuel. At present these adaptations can already be technically carried out but to avoid the economic cost entailed by a complete change, biodiesel is only added up to a 5% to conventional diesel. Another drawback of biodiesel is that an extended or inappropriate storage can promote its decomposition and the release of fatty acids. These acids are not completely soluble in the mix and the formation of solids may cause problems in ducts and filters, as well as the possible corrosion caused by its acidic properties. However, the main reason why biodiesel cannot replace conventional diesel in the future is the origin of the former. Vegetable oil is obtained mainly from crop plants which makes it compete for arable land. This means that at the end the biodiesel production competes with food production, causing a significantly increase in the price of some basic foodstuffs.

To avoid competition with food production a second generation of biofuels has been developed, which must avoid plants, turnips, seeds, tubers, etc. having direct use as food and, in general, any plant biomass requiring arable land. On this basis it is intended to develop second generation biofuels from cellulose or hemicellulose that may come from wood (wood chips or sawdust) but also from any kind of plant biomass waste.

Possible solutions to the problem of the second-generation biofuels production have been recently suggested. In the process described by J. A. Dumesic et al. (*Science* 2005, 308, 1446-1450; PTC Int. Appl. WO2008151178, 2008; US Patent 20090124839, 2007) the aldol condensation of 5-hydroxymethylfurfural (HMF; or furfural) is carried out to produce molecules with 9, 12 or 15 carbon atoms (see scheme 1) that in subsequent steps can be hydrogenated to their corresponding alkanes. This technology has several drawbacks. For example the fact that the aldol condensation needs a second starting material, since an aldol condensation of the HMF or furfural with itself is not possible, whereby it is necessary to carry out a crossed aldol condensation. To this end, Dumesic and collaborators use acetone as a connector of two furanic molecules. However, a crossed aldol condensation involves, because of its nature, a lower selectivity, since acetone can, in fact, condense with itself.

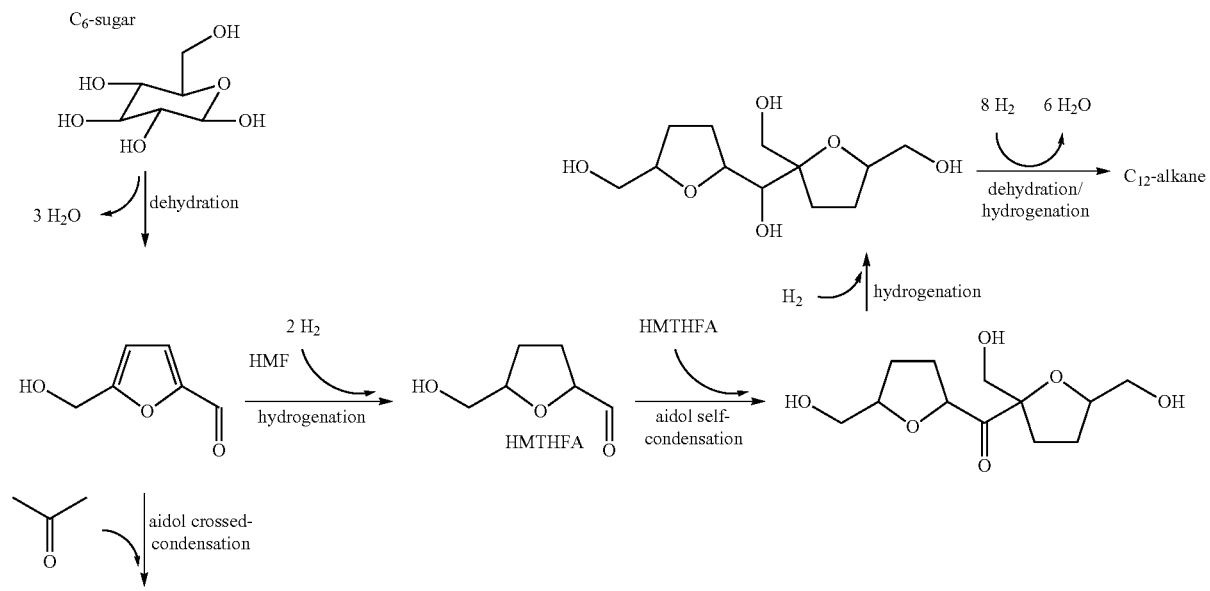

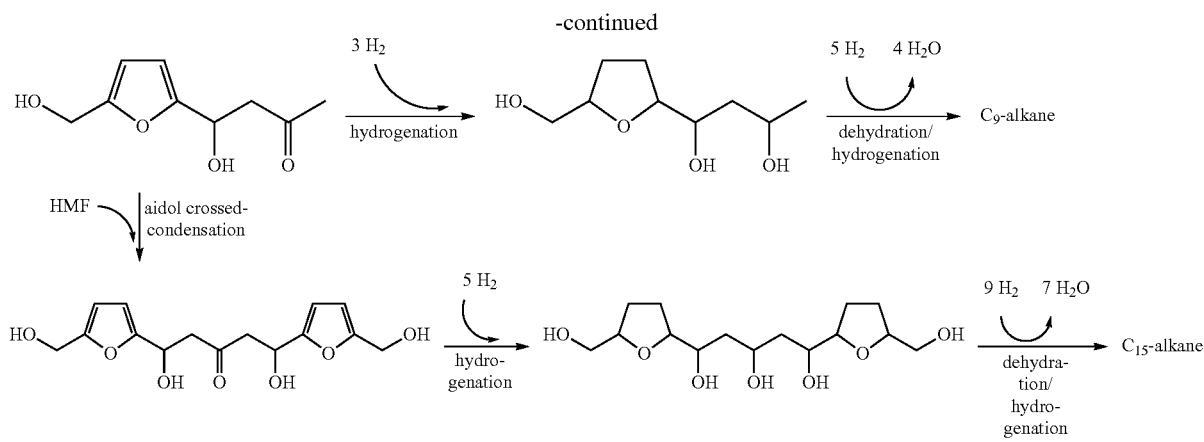

-continued

This has as a consequence that if stoichiometric ratios are used, which means 2 moles of furfural and 1 mole of acetone (since acetone can react by both ends), between 16% and 37% of components with only 5 carbon atoms would be obtained, having a very limited interest as components for gasoline (*Appl. Catal. B Environ.* 2006, 66, 111-118). A second product with 8 carbon atoms which tends to be one-third of the mixture appears under other conditions. This condensation product is hydrogenated to n-octane which does not have an interesting application in gasoline since it has linear chain, nor in diesel because of the low molecular weight. To increase selectivity to 85% with a 71% yield, the condensation has to be carried out in an aqueous phase and hydrogenation in hexadecane as a solvent at 120° C. thereby making the process more expensive (*Appl. Catal. B Environ.* 2006, 66, 111-118). The authors themselves realized the disadvantages caused by selectivity and proposed as an alternative the hydrogenation of the furan ring to tetrahydrofuran since these derivatives are capable of carrying out an aldol condensation with themselves and this would ensure a high selectivity. However, chemoselective hydrogenation of, for example, furfural to tetrahydrofurfural in one step is still a challenge and it is currently carried out in several stages. In any case, if a multistage process is accepted, molecules with a total of 10 carbon atoms can be obtained (*Science* 2005, 308, 1446-1450) as well as by the formation of furoin.

An alternative solution for the second-generation biofuels production is described in R. D. Cortright, WO2008109877, 2007; *Int. Sugar J.* 2008, 110, 672-679, producing in a first step mixtures of compounds with 4 carbon atoms or more from compounds oxygenated in aqueous solution in the presence of a deoxygenation catalyst and a condensation catalyst (Aqueous Phase Reforming). In order to obtain high levels of alkanes the inventors use basic catalysts to condense ketones and aldehydes such as in the case of Dumesic or the oligomerization of alkenes. However their way to combine molecules with low number of carbons is not enough to give molecules with a sufficient number of carbon atoms to be used as Diesel. Thus, the content in raw products of molecules with ten carbon atoms or more is below 50%. FIG. 1 shows the Cortright process, adapted from *Int. Sugar J.* 2008, 110, 672-679.

In other attempts to convert biomass into fuels, oxygenated products are obtained. These do not meet the requirement demanded for the second-generation biofuels such that they can be used in engines currently in use and could, perhaps, be used as additives which can only be added to fuel in limited concentrations. Examples of these can be 2,5-dimethylfuran (*Nature*, 2007, 447, 982-986), or ethers or esters of 5-hydroxymethylfurfural (PCT Int. Appl. WO2009030510, 2007).

Dumesic (*Angew. Chem. Int. Ed.* 2007, 46, 7164-7183), in addition to the process explained above with the key step of aldol condensation, describes other processes such as dehydration and hydrogenation of sorbitol or xylitol to light linear alkanes. However, this latter process cannot be considered as an alternative to produce hydrocarbons increasing the number of carbon atoms to more than the initial five or six (see also *Angew. Chem. Int. Ed.* 2004, 43, 1549-1551).

The present invention refers to a procedure for transforming the biomass-derived products in good quality diesel.

BRIEF DESCRIPTION OF THE DRAWING

FIG. 1 illustrates the Cortright process.

DESCRIPTION OF THE INVENTION

The present invention relates to a procedure for the production of a fuel with a high content in alkanes and low content in oxygenated compounds comprising at least:
  a first alkylation step of 2-methylfuran (commonly known as Sylvan) with a furanic alcohol 2 with the formula:

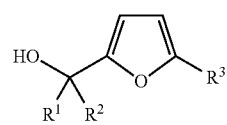

where
  $R^1$ is H or an aliphatic or aromatic or heteroaromatic moiety,
  $R^2$ is H or an aliphatic or aromatic or heteroaromatic moiety and
  $R^3$ is H, hydroxymethyl or an aliphatic or aromatic or heteroaromatic moiety
    in the presence of a catalyst
    a second step of dehydration and hydrogenation of the compound obtained in step 1 in the presence of hydrogen, using suitable dehydration and hydrogenation catalysts.

According to the present invention, the mixture of alkanes of the product can be modified varying the employed reagents. In the first step described previously, the alkylation reaction of a furan (substituted) with another furan compound is used and thus molecules with at least nine connected carbon atoms are obtained. The second step of the procedure of the present invention, is the hydrogenation/dehydration of the product obtained in step 1, to give hydrocarbons that may contain one or several ramifications. In order to achieve a narrow range in the number of carbons in the final product, it is important that the process will be highly selective in the two steps of the reaction.

It should be noted that trying to produce alkylation or hydroxy alkylation of furfural or furfuryl alcohol does not give a product usable for fuels because both molecules under reaction conditions tend to polymerize, forming high molecular weight products (see for example *Makromol. Chem., Rapid Commun.* 1992, 13, 517-523). To avoid these polymerizations using biomass under alkylation/hydroxy alkylation conditions, in the present invention is used 2-methylfuran as the only furanic compound or in a mixture with other furanic compounds in such concentration that the level of polymerization does not harm the economy of the process.

The starting compound 2-methylfuran or "Sylvan" can be obtained, for example, as a by-product in the production of furfuryl alcohol by hydrogenation of furfural in vapour phase at 135° C. using a copper chromite catalyst (K. J. Zeitsch, The chemistry and technology of furfural and its many by-products, Elsevier, Amsterdam, 2000, p. 229). 2-methylfuran can also be obtained with the same catalyst by raising the reaction temperature to 250° C. and increasing the ratio of hydrogen to furfural to 6:1. Under these conditions a 2-methylfuran yield of up to 92.5% can be obtained (L. E. Schniepp, H. H. Geller, R. W. von Korff, *J. Am. Chem. Soc.* 1947, 69, 672-674).

This direct synthesis of 2-methylfuran from pentoses (or furfural) converts this molecule into a starting material suitable for the production of second-generation biofuels such and as described in the present invention.

If only 2-methylfuran and an aldehyde are used in the first step of the production of second-generation biofuels, an intermediate compound is obtained that, after a complete hydrogenation/dehydration, produces undecane (which may have an additional alkyl moiety in C six position). Aldehydes can be easily obtained from primary alcohols by dehydrogenation or selective oxidation, both in the presence of suitable catalysts.

Hydroxyalkylfuranes may come from an alternative source, for example, from furfural derivatives. Thus, for example, 5-methyl furfural can be hydrogenated for obtaining 5-methyl furfuryl alcohol. 5-methyl furfural can be obtained from biomass by hydrogenation of an intermediate product from biomass (see for example *Angew. Chem. Int. Ed.* 2008, 47, 7924-7926). The product obtained in the alkylation of 2-methylfuran with 5-methyl furfuryl alcohol is the same that is formed in the alkylation step from two moles of 2-methylfuran and one mole of formaldehyde with eleven atoms of carbon in the chain.

N-undecane has a boiling point of 196° C. so it can be considered as kerosene or light diesel. The boiling point of the final mix can be increased by introducing a branch, thus increasing the number of carbon atoms. For example the use of butanal together with 2-methylfuran can produce 6-propylundecane with a boiling point of approximately 225-230° C., which due to this property can be used as kerosene and diesel. In this case n-butanal would be obtained by oxidation of n-butanol which can also be a product derived from biomass. The number of carbons may be increased to 16 using 5-methyl furfural with 2 moles of 2-methylfuran. 5-Methyl furfural can be obtained from biomass by hydrogenation of an intermediate product from biomass (see for example *Angew. Chem. Int. Ed.* 2008, 47, 7924-7926). Another isomer with 16 carbon atoms can be obtained by using in the alkylation step two moles of 2-methylfuran and one mole of 2,5-di(hydroxymethyl)furan. The latter can be produced by selective hydrogenation of 5-hydroxymethylfurfural (HMF) that also comes from biomass.

The second step of the procedure of the present invention is a hydrogenation/dehydration of the obtained product after the alkylation (step 1) to give hydrocarbons that may contain one or several branches. Precursors for the hydrogenation/dehydration to long chain alkanes can be achieved, for example, by using 2-hydroxymethylfurfural with three moles of 2-methylfuran. In this way a final molecule with 21 carbon atoms can be obtained.

In the procedure of the present invention, furanic alcohol 2 may come from an external source or it can be formed "in situ" during the reaction either in one or several steps.

Preferably, the product obtained in step 1 has a 2-(furanylmethyl)-5-methylfuran 5 structure:

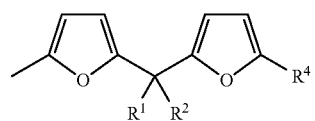

5 where
R$^1$ is H or an aliphatic or aromatic or heteroaromatic moiety,
R$^2$ is H or an aliphatic or aromatic or heteroaromatic moiety and
R$^4$ is H, an aliphatic or aromatic or heteroaromatic moiety.

According to a particular embodiment, the furanic alcohol is synthesized during the reaction from one or several furanic compounds 3 and one or several molecules with a carbonyl group 4

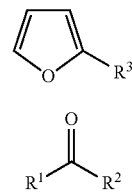

3

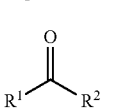

4 where
R$^1$ is H or an aliphatic or aromatic or heteroaromatic moiety,
R$^2$ is H or an aliphatic or aromatic or heteroaromatic moiety and
R$^3$ is H, hydroxymethyl or an aliphatic or aromatic or heteroaromatic moiety.

According to another particular embodiment of the present invention the furanic compound 2 is synthesized during the reaction from 2-methylfuran and at least one aldehyde or one ketone as a molecule with carbonyl group 4.

According to another particular embodiment the furanic compound 2 is synthesized during the reaction from 2-methylfuran and at least one aldehyde selected from the group consisting of formaldehyde, acetaldehyde, propanal, butanal, pentanal, hexanal, heptanal, 4-oxopentanal, furfural, 5-methyl furfural, 5-hydroxymethylfurfural and mixtures thereof.

According to another particular embodiment the furanic compound 2 is synthesized during the reaction from a sugar selected from the group consisting of natural pentoses, natural hexoses and their precursors.

According to another particular embodiment the furanic compound 2 is synthesized during the reaction or previously from a furanic aldehyde by selective hydrogenation of the carbonyl group to a primary alcohol in the presence of a catalyst.

According to another particular embodiment the furanic aldehyde, that is used as substrate for hydrogenation during the reaction or previously, is selected from the group consisting of furfural, 5-methyl furfural and 5-hydroxymethylfurfural group.

According to another particular embodiment the catalyst used for hydrogenation during the reaction in the alkylation step, at the same time incorporates active sites for selective hydrogenation and for alkylation.

In addition, according to the present invention, the furanic compound 2 is preferably selected from the group consisting of furfuryl alcohol, 5-methyl furfuryl alcohol, 2,5-di(hydroxymethyl)furan, alpha-methyl-2-furanmethanol, alpha,5-dimethyl-2-furanmethanol, alpha-ethyl-5-methyl-2-furanmethanol, 5-methyl-alpha-propyl-2-furanmethanol and mixtures thereof.

According to a preferred embodiment, the alkylation of step 1 is carried out at a temperature between 0° C. and 100° C., more preferably between 0° C. and 65° C. and during a contact time between 2 minutes and 48 hours more preferably between 10 minutes and 15 hours, while the hydrogenation/dehydration of step 2 is carried out preferably at a temperature between 200° C. and 450° C., more preferably between 220° C. and 400° C. and during a contact time between 2 minutes and 48 hours more preferably between 10 min and 15 hours.

Moreover, preferably the hydrogenation of step 2 is carried out at a hydrogen pressure between 0.1 bar and 100 bar, preferably between 3 bar and 60 bar.

In the present invention, the alkylation catalyst used in step 1 is preferably a soluble or insoluble acid. The hydrogenation catalyst used in step 2 can contain preferably at least one of the elements selected from the group consisting of Re, Pd, Ru, Pt, Rh, Ni and Cu. The dehydration catalyst also used in the second step is preferably aluminium oxide which in turn can act as a support of the hydrogenating component of the catalyst. In this way, according to a preferred embodiment, the catalyst of the second comprises at least the hydrogenating and the dehydrating.

The main advantage of the procedure according to the present invention is its flexibility with regard to the final product, making possible its election according to the use that it is going to be given to it. Depending on the mixture used in the alkylation/hydroxy alkylation reaction the obtained fuel can be used as kerosene, diesel or destine it to other fractions. This possible selection of the number of carbon atoms of the final product represents an advantage over what is described by Dumesic and Cortright mentioned above. The method allows obtaining mixtures of alkanes with a high content of molecules of 11 and more carbon atoms.

Another advantage of the present procedure is its flexibility with regard to the starting material since it is possible to use biomass from different sources as that obtained from pentoses, hexoses or from other sources. Another added advantage of the present procedure from the ecological and economic point of view is that it does not need any solvent for carrying out the same. In addition, the only by-product that is formed in the alkylation/hydroxy alkylation or in the hydrogenation/dehydration is water.

Throughout the description and claims the word "comprises" and its variants are not intended to exclude other technical characteristics, additives, components or steps. For the skilled in the art, other objects, advantages and characteristics of the invention will derive in part from the description and in part from the practice of the invention. The following examples are provided by way of illustration, and are not intended to be limiting of the present invention.

EXAMPLES

Non-limiting examples of the present invention will be described below.

Example 1

Preparation of a Chemoselective Hydrogenation Catalyst A

A pore volume of 2.98 g of a USY zeolite (particle size 0.425-0.850 mm) with a Si/Al ratio of 20 is impregnated with 4 ml of an aqueous solution of 139 mg of $La(NO_3)_3.6H_2O$ and 722 mg of $Cu(NO_3)_2.3H_2O$. This material is dried in an oven overnight at 60° C.

Example 2

Preparation of a Chemoselective Hydrogenation Catalyst B

A pore volume of 3.00 g of a Beta zeolite (particle size 0.425-0.850 mm) with a Si/Al ratio of 13 is impregnated with 4 ml of an aqueous solution of 139 mg of $La(NO_3)_3.6H_2O$ and 719 mg of $Cu(NO_3)_2.3H_2O$. This material is dried in an oven overnight at 60° C.

Example 3

Preparation of a Hydrogenation/Dehydration Catalyst C

Norit activated carbon particles from 0.425 to 0.850 mm are impregnated with a solution of platinum hexachloride acid hexahydrate in deionised water at pore volume to obtain a catalyst with a platinum concentration of three percent by weight. The material is dried at 60° C. for 72 hrs in an oven.

Example 4

Preparation of a Hydrogenation/Dehydration Catalyst D

Gamma alumina particles from 0.425 to 0.850 mm are impregnated with a solution of platinum hexachloride acid hexahydrate in deionised water at pore volume to obtain a catalyst with a platinum concentration of three percent by weight. The material is dried at 60° C. for 72 hrs in an oven.

Example 5

Reactor for a Chemoselective Hydrogenation Reaction

In a stainless steel tube with an internal diameter of 0.46 cm and 24 cm in length are placed in the following order 0.50 g of silicon carbide, as catalytic bed 1.00 g of catalyst A or B and then 0.50 g of silicon carbide.

Example 6

Reactor for a Hydrogenation/Dehydration Reaction

In a stainless steel tube with an internal diameter of 0.7 cm and 17 cm in length are placed in the following order 0.50 g of silicon carbide, as catalytic bed 2.50 g of catalyst C and 0.50 g of catalyst D and then 0.50 g of silicon carbide.

Example 7

Synthesis of 2,2'-butylidenebis[5-methylfuran]

2-methylfuran (120 g, 1.46 mol), butanal (20 g, 0.279 mol) and para-toluenesulfonic acid (4.00 g, 23.3 mmol) were mixed at room temperature. The mixture was stirred for 1.3 hours and the phases were separated. The organic phase was concentrated and after vacuum distillation (120° C./8 Torr) 2,2'-butylidenebis[5-methylfuran] with a yield of 88% (53.6 g, 0.246 mol) with respect to butanal.

$^1$H RMN (300 MHz, CDCl$_3$) 5=5.93 (d, J=3.0, 2H), 5.89-5.83 (m, 2H), 3.95 (t, J=7.6, 1H), 2.26 (d, J=0.9, 6H), 1.93 (ddd, J=9.7, 7.7, 5.6, 2H), 1.42-1.22 (m, 2H), 0.93 (t, J=7.3, 3H). —$^{13}$C RMN (75 MHz, CDCl$_3$) δ=154.18, 150.57, 105.99, 105.87, 77.45, 77.23, 77.02, 76.60, 38.72, 35.15, 20.60, 13.85, 13.58.

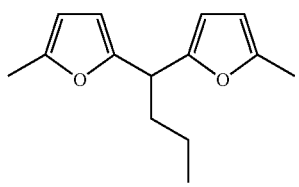

Example 8

Synthesis of 2,2'-butylidenebis[5-methylfuran]

2-methylfuran (247 g, 3.00 mol), butanal (106 g, 1.46 mol) and para-toluenesulfonic acid (8.00 g, 46.6 mmol) were mixed at room temperature. The mixture was stirred for 2.5 hours a 50° C. and the phases were separated The organic phase was concentrated and after vacuum distillation (109° C./1 Torr) 2,2'-butylidenebis[5-methylfuran] with a yield of 79% (254 g, 1.16 mol) with respect to butanal.

Example 9

Synthesis of 2,2'-ethylidenebis[5-methylfuran]

Applying the procedure of example 8, 2,2'-ethylidenebis [5-methylfuran] with a yield of 78% (227 g, 1.20 mol) with respect to etanal was obtained from 2-methylfuran (246 g, 2.99 mol) and etanal (67.9 g, 1.54 mol) in the form of para-acetaldehyde after vacuum distillation (94° C./1 Torr).

$^1$H RMN (300 MHz, CDCl$_3$) 5=6.18-5.46 (m, 4H), 4.12 (q, J=7.2, 1H), 2.27 (d, J=0.6, 6H), 1.57 (d, J=7.2, 3H). —$^{13}$C RMN (75 MHz, CDCl$_3$) δ=155.1, 150.7, 105.9, 105.4, 33.1, 18.2, 13.5.

Example 10

Synthesis of 2,2',2"-methylidinetris[5-methylfuran]

Applying the procedure of example 8 2,2',2"-methylidinetris[5-methylfuran] with a yield of 68% (105 g, 0.410 mol) with respect to 5-methyl furfural was obtained from 2-methylfuran (120 g, 1.46 mol), 5-methyl furfural (80.0 g, 0.727 mol) and para-toluenesulfonic acid (4.00 g, 23.3 mmol) after vacuum distillation (145° C./1 Torr).

$^1$H RMN (300 MHz, CDCl$_3$) 5=5.98 (d, J=3.0, 3H), 5.92-5.88 (m, 3H), 5.37 (s, 1H), 2.27 (d, J=0.5, 9H). —$^{13}$C RMN (75 MHz, CDCl$_3$) δ=151.4, 150.7, 107.7, 106.2, 39.1, 13.5.

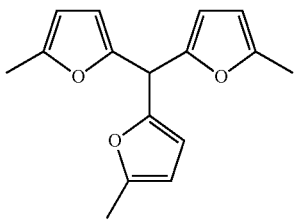

Example 11

Synthesis of 2-(di-(5-methyl-2-furanyl)methyl)-5-(5-methyl-2-furanylmethyl)furan from 5-hydroxymethylfurfural A mixture of 0.52 g of 5-hydroxymethylfurfural, 3.0 g of 2-methylfuran, 0.22 g of dodecane and 58 mg of para-toluenesulfonic acid was heated at 50° C. After 20 hrs was obtained a mixture of products with a main product content of 67% (gas chromatography) with a molecular mass of 336 corresponding to O$_{21}$H$_{20}$O$_4$, the formula of 2-(di-(5-methyl-2-furanyl)methyl)-5-(5-methyl-2-furanylmethyl)furan.

MS m/z (%): 336(74) [M]$^+$, 43(100), 95(61), 175 (19), 198(14), 199(29), 213(28), 241(34), 293(23), 337(16).

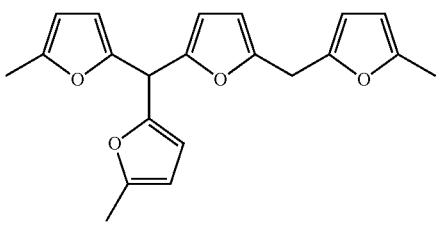

Example 12

Synthesis of 2-(di-(5-methyl-2-furanyl)methyl)-5-(5-methyl-2-furanylmethyl)furan from fructose A mixture of 0.31 g of fructose, 3.0 g of 2-methylfuran, 0.30 g of tetraethylamonio bromide, 0.20 g de dodecane and 0.11 g de para-toluenesulfonic acid was heated at 50° C. After 23 hrs was obtained a mixture of products with a main product content of 69% (gas chromatography) with a molecular mass of 336 corresponding to C$_{21}$H$_{20}$O$_4$, the formula of 2-(di-(5-methyl-2-furanyl)methyl)-5-(5-methyl-2-furanylmethyl)furan.

Example 13

Selective Hydrogenation of 5-Methyl Furfural

A mixture of 5-methyl furfural and 2-methylfuran (1:5) was passed through the reactor prepared in example 5 with catalyst A with a hydrogen pressure of 20 bar at a reaction temperature of 160° C. and it was obtained a mixture of products with 80-88% of 5-methyl furfuryl alcohol and 0.5-5.9% of 2,5-dimethylfuran at a conversion of 5-methyl furfural between 89 and 97%.

Example 14

Selective Hydrogenation of 5-Methyl Furfural and Alkylation

A mixture of 5-methyl furfural and 2-methylfuran (1:5) was passed through the reactor prepared in example 5 with catalyst B with a hydrogen pressure of 20 bar at a reaction temperature of 180° C. and it was obtained a mixture of products with 83% of 2,2'-methylideno[5-methylfuran] at a conversion of 5-methyl furfural of 76%.

Example 15

Hydrogenation/Dehydration of 2,2'-butilidenebis[5-methylfuran]

The organic compound prepared in examples 7 and 8 was passed through the reactor prepared in example 6 with a hydrogen pressure of 30 bar at a reaction temperature of 350° C. and it was obtained a mixture containing 12% of nonane, 4% of an isomer $C_{12}H_{26}$ and 69% of 6-propylundecane. In the sum there was in the mixture of the product more than 85% of alkanes which can serve as kerosene and diesel.

6-propylundecane: $^{13}$C RMN (75 MHz, $CDCl_3$) δ=37.2, 36.2, 33.8, 32.5, 26.5, 22.8, 19.9, 14.5, 14.1.

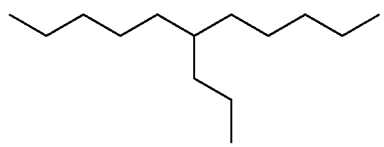

Example 16

Hydrogenation/Dehydration of 2,2'-ethylidenebis[5-methylfuran]

The organic compound prepared in example 9 passed through the reactor prepared in example 6 with a hydrogen pressure of 30 bar at a reaction temperature of 350° C. and it was obtained a mixture containing 6% of heptane, 6% of an isomer $C_{10}H_{22}$ and 65% of 6-methylundecane. In the sum there was in the mixture of the product 77% In the sum there was in the mixture of the product I.

6-methylundecane: $^{13}$C RMN (75 MHz, $CDCl_3$) δ=37.1, 32.8, 32.3, 26.8, 22.7. 19.6. 14.0.

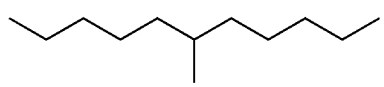

The invention claimed is:
1. A procedure for the production of a fuel wherein it comprises at least:
   a) A first step of alkylation of 2-methylfuran in the presence of a catalyst with a furanic alcohol 2 with the formula:

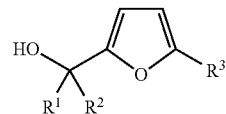

where
   $R^1$ is H or an aliphatic or aromatic or heteroaromatic moiety,
   $R^2$ is H or an aliphatic or aromatic or heteroaromatic moiety and
   $R^3$ is H, hydroxymethyl or an aliphatic or aromatic or heteroaromatic moiety
   b) A second step of catalytic hydrogenation and dehydration of the compound obtained in a).

2. A procedure according to claim 1, wherein the furanic alcohol 2 can be selected from an external source, or it can be formed "in situ" during the reaction in one or several steps.

3. A procedure according to claim 1, wherein the product obtained in the first step has a structure of 2-(furanylmethyl)-5-methylfuran 5:

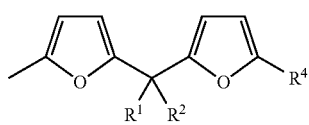

where
   $R^1$ is H or an aliphatic or aromatic or heteroaromatic moiety,
   $R^2$ is H or an aliphatic or aromatic or heteroaromatic moiety and
   $R^4$ is H, an aliphatic or aromatic or heteroaromatic moiety.

4. A procedure according to claim 2, wherein the furanic compound 2 is synthesized during the reaction from one or several furanic compounds 3 and one or several molecules with a carbonyl group 4

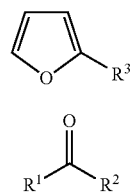

where
   $R^1$ is H or an aliphatic or aromatic or heteroaromatic moiety,
   $R^2$ is H or an aliphatic or aromatic or heteroaromatic moiety and
   $R^3$ is H, hydroxymethyl or an aliphatic or aromatic or heteroaromatic moiety.

5. A procedure according to claim 2, wherein the furanic compound 2 is synthesized during the reaction from 2-methylfuran and at least one aldehyde or one ketone as molecule with carbonyl group 4.

6. A procedure according to claim 2, wherein the furanic compound 2 is synthesized during the reaction from 2-methylfuran and at least one aldehyde selected from the group consisting of formaldehyde, acetaldehyde, propanal, butanal, pentanal, hexanal, heptanal, 4-oxopentanal, furfural, 5-methyl furfural, 5-hydroxymethylfurfural and mixtures thereof.

7. A procedure according to claim 2, wherein the furanic compound 2 is synthesized during the reaction from a sugar selected from the group consisting of natural pentoses, natural hexoses and their precursors.

8. A procedure according to claim 2, wherein the furanic compound 2 is synthesized during the reaction or previously from a furanic aldehyde by selective hydrogenation of the carbonyl group to a primary alcohol in the presence of catalyst.

9. A procedure according to claim 8, wherein the furanic aldehyde is selected from the group consisting of furfural, 5-methyl furfural and 5-hydroxymethylfurfural group.

10. A procedure according to claim 8, wherein the catalyst incorporates at the same time active sites for the selective hydrogenation and for the alkylation.

11. A procedure according to claim 2, wherein the furanic compound 2 is selected from the group consisting of furfuryl alcohol, 5-methyl furfuryl alcohol, 2,5-di(hydroxymethyl) furan, alpha-methyl-2-furanmethanol, alpha,5-dimethyl-2-furanmethanol, alpha-ethyl-5-methyl-2-furanmethanol and 5-methyl-alpha-propyl-2-furanmethanol and mixtures thereof.

12. A procedure according to claim 1, wherein the alkylation of the first step is carried out at a temperature between 0° C. and 100° C. and during a contact time between 2 minutes and 48 hours.

13. A procedure according to claim 12, wherein the alkylation of the first step is carried out at a temperature between 0° C. and 65° C. and during a contact time between 10 minutes and 15 hours.

14. A procedure according to claim 1, wherein the hydrogenation/dehydration of the second step is carried out at a temperature between 200° C. and 450° C. and during a contact time between 2 minutes and 48 hours.

15. A procedure according to claim 14, wherein the hydrogenation/dehydration of the second step is carried out at a temperature between 220° C. and 400° C. and during a contact time between 10 minutes and 15 hours.

16. A procedure according to claim 1, wherein the hydrogenation of the second step is carried out at a hydrogen pressure between 0.1 bar and 100 bar.

17. A procedure according to claim 16, wherein the hydrogenation of the second step is carried out at a hydrogen pressure between 3 bar and 60 bar.

18. A procedure according to claim 1, wherein the alkylation catalyst is an insoluble or soluble acid.

19. A procedure according to claim 1, wherein the hydrogenation catalyst of the second step comprises at least one of the elements Re, Pd, Ru, Pt, Rh, Ni, or Cu or a mixture with two or more of these elements.

20. A procedure according to claim 1, wherein the dehydration catalyst of the second step is aluminium oxide.

21. A procedure according to claim 1, wherein the catalyst of the second step comprises at least one dehydrating function and one hydrogenating function.

22. A procedure according to claim 21, wherein the catalyst of the second step comprises at least one of the elements Re, Pd, Ru, Pt, Rh, Ni, or Cu or a mixture with two or more of these elements and in addition to aluminium oxide.

* * * * *